(12) United States Patent
Donitzky et al.

(10) Patent No.: US 8,465,477 B2
(45) Date of Patent: Jun. 18, 2013

(54) APPARATUS FOR LASER SURGICAL OPHTHALMOLOGY

(75) Inventors: Christof Donitzky, Eckental/Eschenau (DE); Klaus Vogler, Eckental/Eschenau (DE); Olaf Kittelmann, Berlin (DE); Claudia Gorschboth, Nürnberg (DE)

(73) Assignee: Wavelight AG, Erlangen (DE)

( * ) Notice: Subject to any disclaimer, the term of this patent is extended or adjusted under 35 U.S.C. 154(b) by 769 days.

(21) Appl. No.: 12/632,370

(22) Filed: Dec. 7, 2009

(65) Prior Publication Data
US 2011/0137299 A1 Jun. 9, 2011

(51) Int. Cl.
*A61B 18/18* (2006.01)
*A61F 9/00* (2006.01)
*A61F 9/008* (2006.01)
*A61F 2/16* (2006.01)

(52) U.S. Cl.
CPC .............. *A61F 9/008* (2013.01); *A61F 2/167* (2013.01)
USPC .............................................. 606/4; 606/107

(58) Field of Classification Search
CPC .................................. A61F 9/008; A61F 2/167
USPC .......................................... 606/2, 4, 107, 166
See application file for complete search history.

(56) References Cited

U.S. PATENT DOCUMENTS

| 5,549,632 | A | 8/1996 | Lai |
| 2003/0032949 | A1* | 2/2003 | Schuele et al. ............... 606/4 |
| 2003/0153904 | A1 | 8/2003 | Patel |
| 2007/0135805 | A1 | 6/2007 | Peyman |
| 2008/0039769 | A1 | 2/2008 | Peyman |
| 2008/0177256 | A1 | 7/2008 | Loesel |
| 2009/0069794 | A1 | 3/2009 | Kurtz |
| 2009/0069798 | A1 | 3/2009 | Muller et al. |
| 2011/0184393 | A1* | 7/2011 | Brinkmann ............... 606/4 |
| 2012/0172853 | A1* | 7/2012 | Riedel et al. ............... 606/4 |

FOREIGN PATENT DOCUMENTS

| WO | WO 2004/032810 | 4/2004 |
| WO | WO-2011/035793 | 3/2011 |

OTHER PUBLICATIONS

International Searching Authority/European Patent Office, "Notification of Transmittal of the International Search Report and The Written Opinion of the International Searching Authority, or the Declaration," for PCT/EP2009/008747, mailed Aug. 4, 2010, 12 pages.

* cited by examiner

*Primary Examiner* — Huy K Mai
(74) *Attorney, Agent, or Firm* — Haynes and Boone, LLP

(57) ABSTRACT

The present invention relates to an apparatus 10 for ophthalmological laser surgery, with an optical imaging system for imaging a treatment laser beam 14 onto a focal point, with a temperature-measuring device for measuring a temperature assigned to the imaging system, and with an electronic control arrangement (22) connected to the temperature-measuring device, which is configured to control the focal-point setting in a manner depending on the measured temperature. The present invention further relates also to an associated method.

19 Claims, 2 Drawing Sheets

APPARATUS FOR LASER SURGICAL OPHTHALMOLOGY

Figure 1:
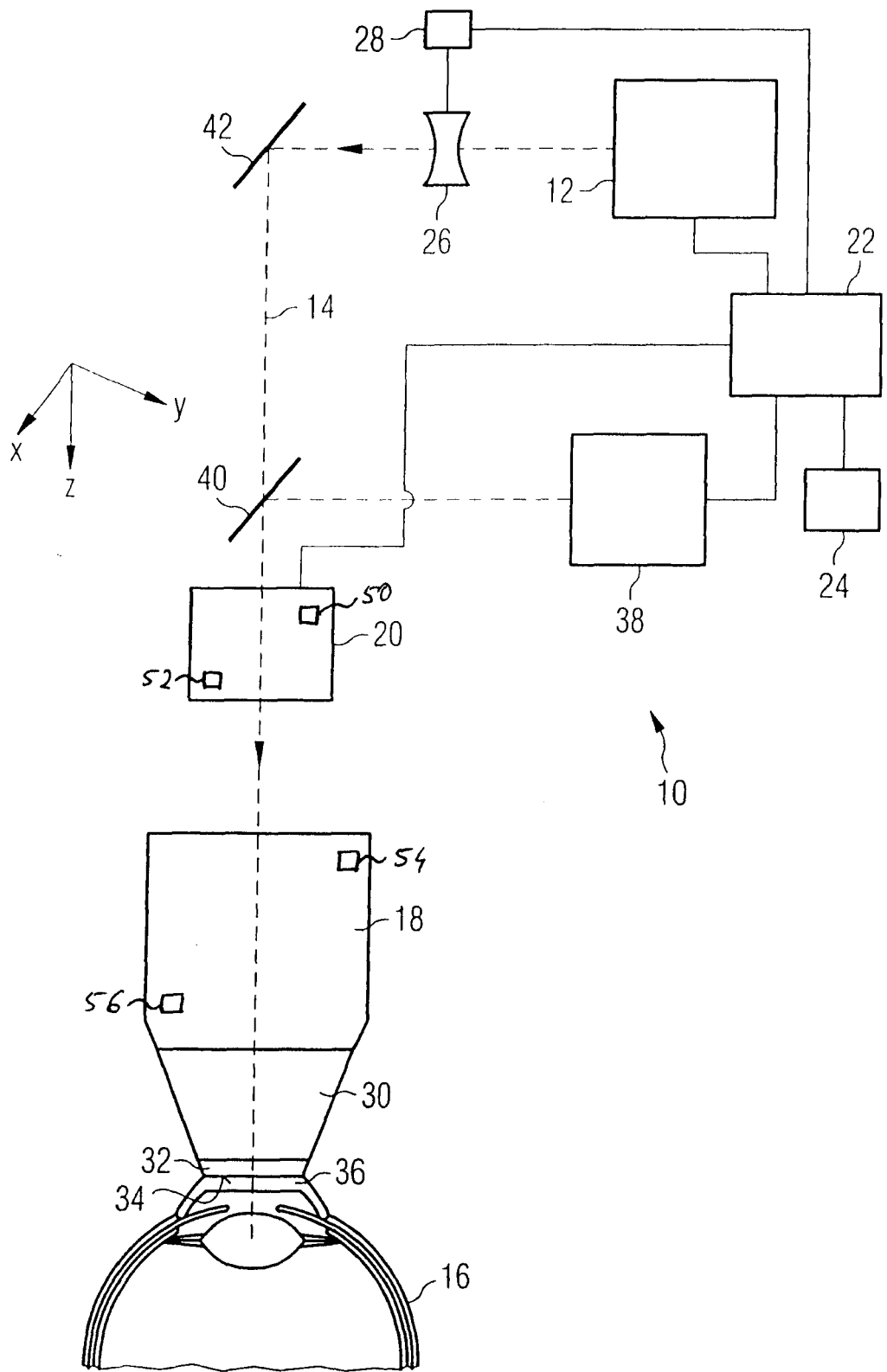

The invention relates to an apparatus for ophthalmological laser surgery and to an associated method.

Pulsed laser radiation finds application in numerous techniques for treating the human eye. Local control of the beam focus of the laser beam in the z-direction (this means, according to conventional notation, the direction of propagation of the laser beam) is always effected with reference to a known reference point or a known reference surface in the coordinate system of the laser apparatus.

Depending on the type of treatment, differing reference points or reference surfaces may serve as reference for the z-control of the beam focus. With some of these techniques the eye to be treated is pressed against a transparent contact element which, with its contact surface facing towards the eye, constitutes a reference surface for the positioning of the beam focus in the z-direction. In particular, treatment techniques that serve for producing incisions in the ocular tissue by means of focused femtosecond laser radiation frequently make use of such contact elements by way of z-reference for the laser focus. By the contact element being pressed against the eye in such a way that a conforming planar abutment of the eye against the contact surface of the contact element facing towards the eye arises, the contact element presets the z-position of the anterior surface of the eye. By referencing of the beam focus in the z-direction in relation to this contact surface of the contact element it is then ensured that the incision or the individual photodisruption (the production of an incision in the human eye by means of pulsed femtosecond laser radiation is normally based on the effect of so-called laser-induced optical break-through, which results in a photodisruption) is situated at the desired position deep within the ocular tissue.

Incisions produced by laser technology occur, for example, in the case of so-called fs LASIK, in which a small anterior cover disc of the cornea, designated in specialist circles as a flap, is cut free by means of femtosecond laser radiation, in order subsequently, as in the case of classical LASIK technology (LASIK: Laser In-Situ Keratomileusis), to fold aside the flap that is still attached to the remaining corneal tissue in a hinge region and to process the tissue exposed in this way in ablating manner by means of UV laser radiation. Another application for the placement of intra-tissue incisions in the ocular tissue is so-called corneal lenticle extraction, in which a small lenticular disc is cut out all round within the corneal tissue by means of femtosecond laser radiation. This small disc is subsequently removed through an additional incision which is guided out to the surface of the eye (the additional incision is produced either by means of a scalpel or likewise by means of femtosecond laser radiation). Also in the case of corneal grafting (keratoplasty) or for other incisions, for example for corneal ring segments, the production of an incision in the cornea can be carried out by means of focused pulsed laser radiation.

For reasons of hygiene, the contact element (applicator) bearing the contact surface is often a disposable article which has to be exchanged before each treatment. Certain manufacturing tolerances cannot normally be ruled out in the production of the contact elements, even with the greatest precision of manufacture. After an exchange of the contact element, therefore, the z-position of the contact surface facing towards the eye may be different—albeit only slightly—from that in the case of the contact element used previously. In the case of laser treatments by means of focused femtosecond laser radiation, focus diameters that are as small as possible are striven for, in order to limit the photodisruptive action locally to be as restricted as possible. Modern instruments operate, for example, with focus diameters within the low single-digit μm range. Often in the course of the implementation of interventions by means of femtosecond systems the depth of the incision in the target tissue has to be defined with extremely high accuracy (incision-depth tolerances <5 μm). As described previously, in such interventions the tissue to be treated and the optical system of the laser are, as a rule, firmly coupled to one another by means of a contact element, in order to obtain the requisite depth of incision with corresponding precision in the z-direction. This demands a correspondingly high accuracy of manufacture of the contact element, which, however, cannot always be guaranteed. Given diminished precision of manufacture of the contact element, the problem therefore arises of an imprecise incision guidance in the corneal tissue in the z-direction—i.e. the manufacturing tolerances for these contact elements enter directly into the inaccuracies for the depth of incision in the tissue.

In the state of the art, use is generally made of applicators that have been manufactured precisely, with corresponding effort. In the course of the installation of these applicators the optical system of the laser is adjusted to the demanded distance between the optical system and the incision plane on the basis of a reference applicator, utilising the interaction between laser radiation and material. This is already known from WO 2004/032810, for example.

The spacing between tissue and laser system, and hence directly the real depth of incision in the tissue, is substantially determined by the dimension of the applicator—i.e. by the real optical length of the applicator in the z-direction. This makes it necessary, for the purpose of obtaining the requisite precision of the depth of incision, that the applicators have to be manufactured with correspondingly small tolerances with respect to their dimension (the relative length accuracy lies clearly <<0.1%), distinctly increasing the production costs of these applicators and having a direct effect, particularly in the case of single-use articles that are required in large numbers, on the costs of treatment and hence on the so-called costs of ownership.

From PCT/EP2009/006879, filed by the present applicant, it is known to take account of and to equalise inaccuracies of manufacture of the contact element. For this purpose, by means of a measuring device a positional surveying of the contact surface relative to the direction of propagation of the treatment laser beam is carried out and by means of an electronic evaluating and control arrangement connected to the measuring device the focal location of the treatment laser beam is adjusted in a manner depending on the measured position data acquired by the measuring device.

Although the procedures known from the state of the art take account of inaccuracies of manufacture of the contact element or attempt to avoid such inaccuracies through precision that is as high as possible (with, at the same time, high costs), they disregard further factors influencing the accuracy of adjustment of the focal point in the z-direction.

In addition to the stated manufacturing tolerances, the effective depth of incision is dependent on temperature drifts of the dimension of the applicator and also on the effective focal length of the overall optical system—i.e. the real optical length of the applicator in the direction of propagation of the treatment laser beam and also the focal length of the optics of a laser system vary in a manner depending on the functional temperature range. Within the conventional functional temperature range of medical instruments of 15° C.-35° C. the stated drifts may easily sum to 30 μm to 50 μm. Hence the incision-depth tolerances of <5 μm being striven for can only be obtained with difficulty or can no longer be obtained.

It is an object of the present invention to make available an apparatus for ophthalmological laser surgery and also an associated method, said apparatus and said method enabling a more precise laser treatment of an eye.

With a view to achieving this object, in accordance with the invention an apparatus for ophthalmological laser surgery is provided that comprises the following components: an optical imaging system for imaging a treatment laser beam onto a focal point, a temperature-measuring device for measuring a temperature assigned to the imaging system, and an electronic control arrangement connected to the temperature-measuring device, which is configured to control the focal-point setting in a manner depending on the measured temperature.

In this connection the apparatus may include a contact surface for the shaping abutment of an eye to be treated and also a radiation-source for providing the treatment laser beam. Furthermore, the imaging system may have optical components for directing the treatment laser beam through the contact surface onto the eye.

The invention enables a control and/or readjustment of a position, for example a preset position, of the laser-beam focus in the z-direction (corresponding to the direction of propagation of the treatment laser beam) in a manner depending on the measured temperature of the critical components crucially influencing the depth of focus (e.g. the objective, the component for beam expansion etc.) and around the apparatus. Presetting of the focal point may be effected in various ways.

The position of the focus in the z-direction may be preset, for example, by the z-position of the contact surface with respect to a given reference point in a fixed coordinate system of the laser-surgical apparatus being known. In this connection use is preferentially made of a patient adapter (applicator), the real optical length of which in the direction of propagation of the treatment laser beam (z-direction) has been established with high accuracy, so that the focal point can be preset to the known length. Changes in the length of the applicator or changes in the effective focal length of the optical components contained in the apparatus by reason of changing temperature around the apparatus can be detected by the temperature-measuring device and taken into account appropriately by the control arrangement. Similarly, it is conceivable that the effective optical spacing (the real optical length) between the surface of the applicator (the contact surface) facing towards the eye and the surface facing away from the eye (the surface facing towards the optical components of the apparatus) has already been measured outside the apparatus and, for example, embossed on the associated applicator via a coding. This coding can then be read out by the apparatus, for example automatically or manually, and relayed to the control arrangement. On the basis of the value that has been read out, the control arrangement can firstly preset the focal point.

Alternatively, for the purpose of presetting the focal point the z-position of the contact surface with reference to the given reference point can be measured. For this purpose the apparatus preferably has a measuring device for positional surveying of the contact surface relative to the direction of propagation of the treatment laser beam. For this purpose the measuring device comprises, for example, a second radiation-source providing a measuring beam. The optical components are then preferentially designed and arranged for the purpose of also directing the measuring beam through the contact surface onto the eye. By means of the measuring beam, the measuring device can preferentially provide measured position data that are representative of the measured position of the contact surface at at least one place on the same and can relay the ascertained measured position data to the control arrangement. In response to this, the electronic control arrangement can preset the focal point in a manner depending on the measured position data. For differing contact elements a differing z-position of the contact surface in the coordinate system or a differing effective optical spacing may result, depending on the accuracy of production. By evaluation of the measurement, carried out by the measuring device, of the z-position of the contact surface and/or of the real optical length of the applicator, firstly the focal point in the z-direction can be preset, so that production inaccuracies are diminished or avoided. On the basis of the measured temperature, the preset focal point can subsequently be adapted or readjusted.

Adaptation or readjustment of the preset focal point may, for example, be effected at predetermined time-intervals by a repeated measurement of the temperature by the temperature-measuring device being effected after predetermined periods of time. For example, a readjustment may be effected when the measured temperature exceeds the previously measured temperature by a predetermined threshold. In such a case a considerable temperature drift would have to be assumed, which necessitates a readjustment of the focal point. A diminution of the predetermined threshold enables a more accurate but more elaborate readjustment of the focal point. The predetermined time-intervals and the predetermined threshold are preferentially saved in a memory connected to the control arrangement, so that the control arrangement can read out these values as required and can control the temperature-measuring device and also the readjustment of the focal point appropriately. It is also conceivable that a renewed temperature measurement is effected only when, for example, an appropriate instruction is input by a user into the temperature-measuring device or into components connected thereto.

The temperature-measuring device may comprise one or more temperature sensors which are arranged on one or more of the optical components and connected to the control arrangement. The optical components preferably constitute, on the one hand, a scan unit for deflecting the treatment laser beam in a plane (x-y plane) orthogonal to the beam path thereof or a 3D scan unit for three-dimensional deflecting of the treatment laser beam and also, on the other hand, focusing optics for focusing the treatment laser beam to the laser-beam focus. In this case, preferentially two temperature sensors in each instance are arranged on the scan unit and on the focusing optics. However, also one temperature sensor or more than two temperature sensors may be arranged in each instance on the scan unit and on the focusing optics.

For the purpose of adapting the focal point, the optical components comprise at least one controllable optical element. For example, the controllable optical element is constituted by a lens that is positionally variable in the direction of propagation of the treatment laser beam. For the purpose of controlling the lens, the control arrangement can generate, as a function of the measured temperature, an actuating variable for readjusting the preset focal point. The lens is, for example, mechanically displaceable or repositionable along the optical beam path. In this case the control arrangement has preferably been set up to vary the position of the positionally variable lens by the ascertained actuating variable for the purpose of adapting the focal point.

Alternatively, it is conceivable to use a controllable liquid lens of variable refractive power. With unchanged z-position and also otherwise unchanged setting of the focusing objective, a z-shift of the beam focus can be obtained by displacing a longitudinally adjustable lens or by variation of the refractive power of a liquid lens, in order thereby to adapt the focal point to the altered temperature. It will be understood that for the purpose of z-adjustment of the beam focus other components are also conceivable, such as a deformable mirror for instance.

The control arrangement may further have a memory unit or may be connected to such a unit in which the dependence of the focal point on the temperature is stored as a function. The temperature dependences of all the materials used in the apparatus and of all the spacings occurring in the apparatus (for example, the spacings of the optical components from one another or the real optical length of the applicator) can be used in order to calculate a temperature sensitivity of the effective focal length of the optical components starting from a reference temperature. The temperature sensitivity is preferentially ascertained and recorded separately for the scan unit and the focusing optics, but it may also be calculated for these jointly. The ascertained temperature sensitivity may be saved as a family of curves in the memory unit and, as required, may be interrogated by the control arrangement and used for the purpose of adapting the focal point on the basis of the stored family of curves.

By virtue of the temperature being taken into account in the readjustment of the focal point of the treatment laser beam by the control arrangement, changes in the effective focal length as well as changes in the effective optical spacing of the applicator occurring by reason of fluctuations in temperature are compensated. By this means, it is ensured that an incision pattern or, to be more exact, a pattern of photodisruptions to be realised in the eye is in fact situated at the desired place deep within the eye (that is to say, at the desired place in the z-direction). In this manner, highly precise depths of incision are possible, for example in the case of the production of a LASIK flap, in the case of corneal lenticle extractions or in cases of keratoplasty.

The control arrangement may furthermore be configured to generate, in the course of the readjustment of the focal point in the z-direction at several different places in an x-y plane orthogonal to the z-direction, differing actuating variables for the controllable optical element. As a result, it is possible, for example, to compensate individually variably strong effects of the changes in temperature on the position of the contact surface in the x-y plane.

The measuring device is preferentially an optical-coherence interferometric measuring device and possesses to this end an optical interferometer.

The contact surface will frequently be part of an exchangeably arranged disposable component, for example a single-use applicator. However, it is to be emphasised that the invention does not presuppose a disposable nature of the element bearing the contact surface. The invention is equally employable in configurations with a permanently incorporated or at least repeatedly usable contact surface.

The contact surface is preferably constituted by a transparent applanation plate or a transparent contact lens. Applanation plates possess, at least on their flat side facing towards the eye, a plane applanation face with which a levelling of the front of the eye is achieved. The use of applanation plates for the purpose of referencing the eye to be treated is normally favourable from the point of view of a high beam quality of the laser radiation. Nevertheless, within the scope of the invention it is equally possible to use by way of contact element a contact lens with a, typically, concavely or convexly shaped lens surface facing towards the eye. The advantage of such contact lenses is, for example, a smaller rise in the intraocular pressure when pressing onto the eye.

In a preferred configuration the contact surface is constituted by a transparent contact element which is part of a patient adapter which is coupled, in particular exchangeably coupled, with a focusing objective of the apparatus.

According to a further aspect, in accordance with the invention a method for controlling a focal point of a treatment laser beam for ophthalmological laser surgery is furthermore provided, comprising the following steps:
  imaging a treatment laser beam onto a focal point by means of an imaging system,
  measuring a temperature assigned to the imaging system, and
  controlling the focal-point setting in a manner depending on the measured temperature.

The method may further comprise the steps of establishing a shaping abutting contact between an eye and a contact surface, and of directing the treatment laser beam through the contact surface onto the eye.

Also in connection with the method aspect, measured position data that are representative of a measured position of the contact surface at at least one place in the same relative to the direction of propagation of the treatment laser beam can be ascertained or read out, as described previously. Irrespective of whether the measured position data were ascertained or read out, the focal point can be preset in a manner depending on the measured position data and, subsequent to this, can be readjusted on the basis of the measured temperature.

Figure 2:
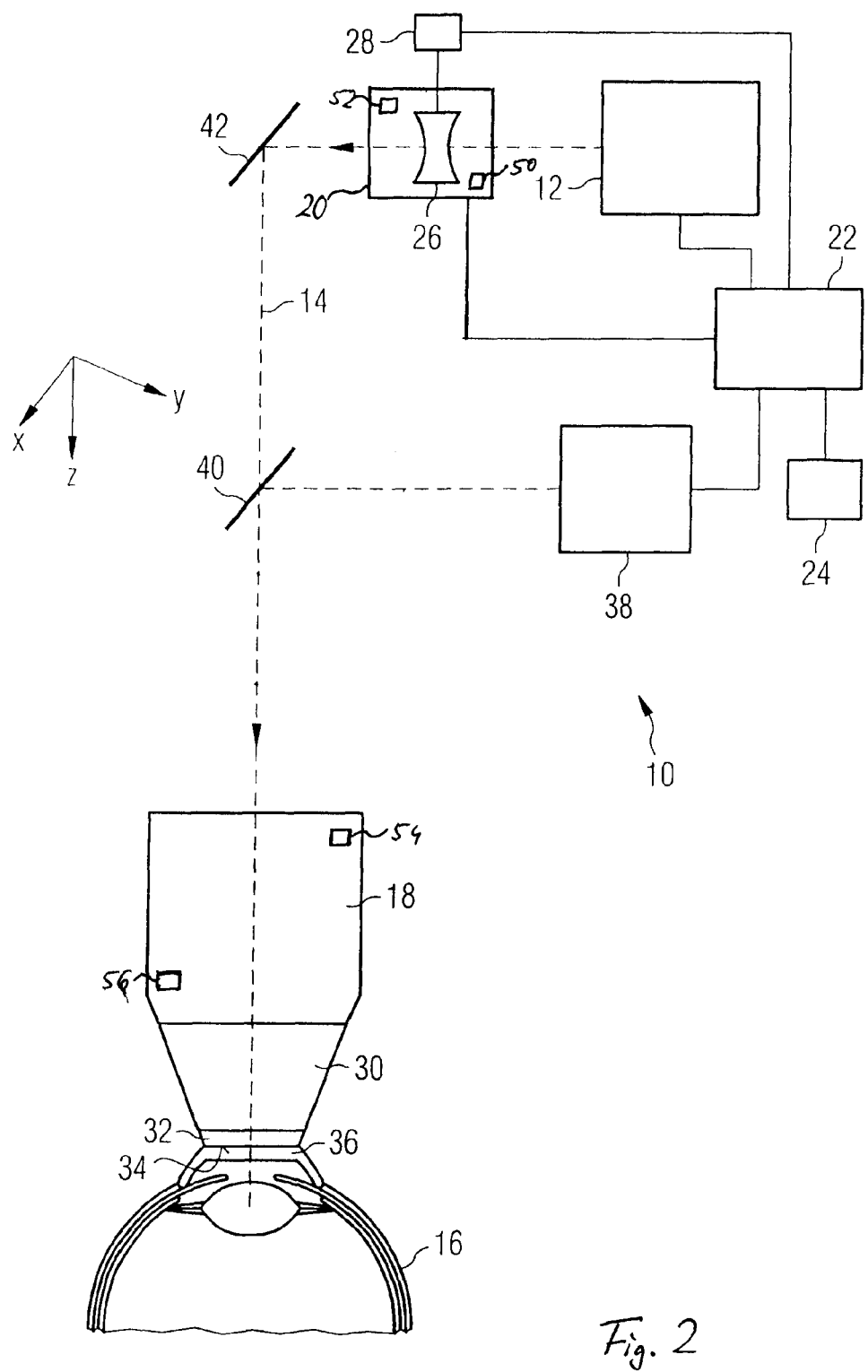

The invention will be elucidated further in the following on the basis of the appended drawings. Shown are:

FIG. 1 in greatly schematised manner, a first exemplary embodiment of an apparatus for ophthalmological laser surgery; and FIG. 2 in greatly schematised manner, a second exemplary embodiment of an apparatus for ophthalmological laser surgery.

The laser-surgical apparatus according to both embodiments is generally denoted by 10.

The laser-surgical apparatus 10 according to the first embodiment has a femtosecond laser (fs laser) 12 which emits pulsed laser radiation with pulse durations within the femtosecond range. The laser radiation propagates along an optical beam path 14 and finally arrives at an eye 16 to be treated. In the beam path 14 various components for guiding and shaping the laser radiation are arranged. In particular, these components include a focusing objective 18 (for example, an f-theta objective) and also a scanner 20 connected upstream of the objective 18, by means of which the laser radiation provided by the laser 12 is capable of being deflected in a plane (x-y plane) orthogonal to the beam path 14. A coordinate system that has been sketched in illustrates this plane and also a z-axis defined by the direction of the beam path 14. The scanner 20 is, for example, constructed in a manner known as such from a pair of galvanometrically controlled deflecting mirrors which are each responsible for the beam deflection in the direction of one of the axes spanning the x-y plane. A central control unit 22 controls the scanner 20 in accordance with a control program stored in a memory 24, which implements an incision profile (represented by a three-dimensional pattern of scan points at which, in each instance, a photodisruption is to be brought about) to be generated in the eye 16.

Moreover, the aforementioned components for guiding and shaping the laser radiation include at least one controllable optical element 26 for z-adjustment of the beam focus of the laser radiation. In the exemplary case that is shown, this optical element is constituted by a lens. A suitable actuator 28, which in turn is controlled by the control unit 22, serves for controlling the lens 26. For example, the lens 26 may be mechanically displaceable along the optical beam path 14. Alternatively, it is conceivable to use a controllable liquid lens of variable refractive power. With unchanged z-position and also otherwise unchanged setting of the focusing objective 18, by displacing a longitudinally adjustable lens or by variation of the refractive power of a liquid lens it is possible to obtain a z-shift of the beam focus. It will be understood that for the purpose of z-adjustment of the beam focus other components are also conceivable, for instance a deformable mirror. On account of its comparatively greater inertia, with the focusing objective 18 it is expedient to undertake only an initial basic setting of the beam focus (i.e. focusing to a predetermined z-reference position) and to effect the z-shifts of the beam focus which are predetermined by the incision profile by means of a component with quicker speed of response which is arranged outside the focusing objective 18. It will be understood that the lens 26 may also be part of the scanner 20, and the scanner 20 formed thereby may be arranged both upstream of and downstream of the semitransmitting deflecting mirror 40. The case in which the lens is part of the scanner 20 and this scanner 20 containing the lens 26 is arranged upstream of the deflecting mirror 42 will be elucidated later with reference to FIG. 2.

On the side of emergence of the beam the focusing objective 18 is coupled with a patient adapter 30 which serves for establishing a mechanical coupling between the eye 16 and the focusing objective 18. Ordinarily in the course of treatments of the type being considered here a suction ring which is not represented in any detail in the drawing but which is known in itself is placed onto the eye and fixed there by suction force. The suction ring and the patient adapter 30 form a defined mechanical interface which permits a coupling of the patient adapter 30 onto the suction ring. In this regard, reference may be made, for example, to international patent application PCT/EP2008/006962, the total content of which is hereby incorporated by reference.

The patient adapter 30 serves as carrier for a transparent contact element 32 which, in the exemplary case that is shown, takes the form of a plane-parallel applanation plate. The patient adapter 30 comprises, for example, a taper-sleeve body, at the narrower (in the drawing, lower) sleeve end of which the applanation plate 32 is arranged. In the region of the wider (in the drawing, upper) sleeve end the patent adapter 30 is, on the other hand, attached to the focusing objective 18 and possesses there suitable structures which permit a fixing, if desired a detachable fixing, of the patient adapter 30 to the focusing objective 18.

Because it comes into contact with the eye 16 during the treatment, the applanation plate 32 is a critical article from the point of view of hygiene, which therefore is expediently to be exchanged after each treatment. For this purpose the applanation plate 32 may have been exchangeably fitted to the patient adapter 30. Alternatively, the patient adapter 30 may form, together with the applanation plate 32, a disposable unit, for which purpose the applanation plate 32 may have been undetachably connected to the patient adapter 30.

In any case, the underside of the applanation plate 32, facing towards the eye, forms a plane contact surface 34 against which the eye 16 is pressed in preparation for the treatment. This brings about a levelling of the anterior surface of the eye, with simultaneous deformation of the cornea, denoted by 36, of the eye 16.

In order to be able to utilise the contact surface 34 as a reference for the presetting of the beam focus in the z-direction, it is necessary to know its z-position in the coordinate system of the laser-surgical apparatus. By reason of unavoidable manufacturing tolerances, it cannot be ruled out that in the case of incorporation of varying applanation plates or varying patient adapters 30, which are each equipped with an applanation plate 32, the z-position and, under certain circumstances, also the angular position of the contact surface 34 show more or less significant fluctuations. To the extent that these fluctuations remain disregarded in the z-presetting of the beam focus, undesirable errors arise in the actual position of the incisions in the eye 16 that are produced.

The laser-surgical apparatus 10 therefore includes an optical-coherence interferometric measuring device 38, for example an OLCR measuring device (OLCR: optical low-coherence reflectometry), which emits a measuring beam which by means of an immovably arranged semitransmitting deflecting mirror 40 is coupled into the beam path 14 in which the treatment laser radiation of the laser 12 also travels. The measuring device 38 causes the generated measuring beam to produce interference with a reflection beam coming back from the eye 16. From the measured interference data acquired in this regard, the z-position of the contact surface 34 within the coordinate system of the laser-surgical apparatus can be ascertained. Therefore the measured interference data may also be designated as measured position data. The control unit 22 receives the measured interference data from the measuring device 38 and calculates therefrom the z-position of that place on the contact surface 34 at which the measuring beam impinged or through which the measuring beam passed.

In the exemplary case that is shown, the measuring beam emitted by the measuring device 38 passes through the scanner 20. This makes it possible to utilise the deflecting function of the scanner 20 also for the measuring beam. The scanner module 20 could also contain a second separate scanner solely for the OLCR, which, equipped with smaller mirrors, operates distinctly more quickly.

In the course of the following laser treatment of the eye 16 the control unit 22 takes into account the actual z-position of the contact surface 34 ascertained in this way in connection with the z-control of the beam focus, specifically in such a way that the incision is in fact produced at the intended position deep within the cornea 36. For this purpose the evaluating and control unit 22 references the z-position of the beam focus that is to be set to the measured z-position of the contact surface 34.

By virtue of the previously described procedure, the z-position of the beam focus is, however, only preset, since temperature drifts of the effective focal length of the laser-surgical apparatus 10 and also of the real optical length of the patient adapter 30 in the z-direction are not taken into account. Accordingly, the laser-surgical device 10 has four temperature sensors 50, 52, 54, 56, two of which are arranged on the scanner 20, and two of which are arranged on the focusing objective 18. The temperature sensors measure the real temperature at their corresponding positions and relay the measured temperature values to the control unit 22. Relaying of the temperature values to the control unit 22 may be effected in wireless or wired manner; i.e. the temperature sensors 50 52, 54, 56 may be connected to the control unit 22 in wireless or wired manner. In the exemplary embodiment represented in FIG. 1, in exemplary manner the scanner 20 and hence the temperature sensors 50, 52 arranged on the scanner 20 are connected to the control unit 22 in wired manner, whereas the temperature sensors 54, 56 arranged on the focusing objective 18 are connected to the control unit 22 in wireless manner in order to relay their measured temperature values to the control unit 22 for further processing.

In the memory 24 a temperature sensitivity of the effective focal length is saved as a family of curves, both for the scanner 20 and for the focusing objective 18. Given the existence of a new measured temperature value, the control unit evaluates the associated function and generates a corresponding actuating variable for the purpose of readjusting the preset z-position of the lens 26. Once a temperature value is ascertained by one or both of the temperature sensors 50, 52 fitted to the scanner 20 (in the case of the measurement of two temperature values by the two temperature sensors 50, 52, an average temperature value derived from the two values is used), the temperature sensor relays the measured temperature value to the control unit 22. The latter then searches the memory 20 for the associated temperature sensitivity for the scanner 20, generates therefrom an actuating variable and communicates the latter to the actuator 28 which shifts the lens 26 in the z-direction in accordance with the actuating variable. By virtue of this z-shift of the lens 26, the preset position of the beam focus is readjusted in such a manner that changes in the real optical length of the patient adapter and/or changes in the effective focal length of the laser-surgical apparatus 10, occurring by reason of fluctuations in the real temperature, are also taken into account and compensated.

According to the second embodiment of the laser-surgical apparatus 10 shown in FIG. 2, the scanner 20 comprises the lens 26 which is positionally shiftable in the direction of propagation of the treatment laser beam and is arranged upstream of the deflecting mirror 42 in the direction of propagation of the laser radiation. In this manner the scanner 20 is a 3D scanner which possesses three-dimensional scan properties, so that the laser radiation can be deflected in any direction (x, y, z) by the 3D scanner 20.

Recording and evaluation of the measured temperature values by means of the temperature sensors 50, 52, 54, 56 and the control unit 22 are effected in a manner analogous to the first embodiment shown in FIG. 1. As distinct from the first embodiment, in the second embodiment shown in FIG. 2 both the presetting of the focal point and the readjustment of the focal point are effected by the 3D scanner 20 which is controlled by the control unit 22.

The invention claimed is:

1. Apparatus for ophthalmological laser surgery, comprising:
    a laser-surgical apparatus configured to direct a treatment laser beam onto a focal point in an eye to be treated;
    a temperature-measuring device for measuring a temperature of an optical component of the laser-surgical apparatus; and
    an electronic control arrangement in communication with the temperature-measuring device and the laser-surgical apparatus, the electronic control arrangement configured to control the focal point of the treatment laser beam based on the measured temperature of the optical component of the laser-surgical apparatus.

2. Apparatus according to claim 1, further comprising a contact element having a contact surface for contacting an outer surface of the eye to be treated.

3. Apparatus according to claim 2, further comprising a measuring device for positional surveying of the contact surface relative to the direction of propagation of the treatment laser beam, the measuring device providing measured position data representative of the measured position of the contact surface within a coordinate system of the laser-surgical apparatus, wherein the electronic control arrangement is configured to preset the focal point of the treatment laser beam based on the measured position data.

4. Apparatus according to any one of the preceding claims, wherein the temperature-measuring device comprises one or more temperature sensors arranged on the optical component of the laser-surgical apparatus.

5. Apparatus according to claim 4, wherein the optical component is a focusing objective.

6. Apparatus according to claim 4, wherein the optical component is a scanner.

7. Apparatus according to claim 6, wherein the scanner is a three-dimensional scanner.

8. Apparatus according to claim 3, further including at least one optical component having at least one controllable optical element for controlling the focal point.

9. Apparatus according to claim 8, wherein the controllable optical element has at least one lens that is positionally variable in the direction of propagation of the treatment laser beam.

10. Apparatus according to claim 9, wherein the control arrangement is configured to generate, for the purpose of controlling the focal point, an actuating variable for varying the position of the positionally variable lens.

11. Apparatus according to claim 8, wherein the control arrangement has a memory unit in which the dependence of the focal point on the temperature is stored as a function and the control arrangement is configured to control the focal point on the basis of the stored function and the measured temperature.

12. Apparatus according to claim 3, wherein the measuring device comprises a radiation-source providing a measuring beam, and includes optical components designed and arranged to direct the measuring beam through the contact surface onto the eye.

13. Apparatus according to claim 3, wherein the measuring device comprises an optical interferometer.

14. Apparatus according to claim 13, wherein the contact surface is part of an exchangeably arranged disposable component.

15. Apparatus according to claim 14, wherein the pulse duration of the treatment laser beam lies within the femtosecond range.

16. Apparatus according to claim 2, wherein the contact element is an applanation plate.

17. Apparatus according to claim 2, wherein the contact element is a contact lens.

18. Method for controlling a focal point of a treatment laser beam for ophthalmological laser surgery, comprising:
    directing a treatment laser beam from a laser-surgical apparatus onto a focal point within an eye to be treated;
    measuring a temperature of an optical component of the laser-surgical apparatus; and
    controlling the focal point of the treatment laser beam based on the measured temperature of the optical component of the laser-surgical apparatus.

19. Method according to claim 18, wherein the method further comprises:
    establishing a shaping abutting contact between an eye and a contact surface of a contact element;
    directing the treatment laser beam through the contact surface onto the eye;
    obtaining measured position data representative of a measured position of the contact surface relative to a coordinate system of the laser-surgical apparatus in the direction of propagation of the treatment laser beam; and,
    presetting the focal point in a manner depending on the measured position data.

* * * * *